(12) United States Patent
Picot et al.

(10) Patent No.: US 12,076,523 B2
(45) Date of Patent: Sep. 3, 2024

(54) SYRINGE ACTUATED STOPCOCK SMART-VALVE

(71) Applicant: Becton, Dickinson and Company, Franklin Lakes, NJ (US)

(72) Inventors: John Picot, Flemington, NJ (US); Hong Zhu, Glen Rock, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 202 days.

(21) Appl. No.: 17/155,297

(22) Filed: Jan. 22, 2021

(65) Prior Publication Data

US 2021/0228859 A1    Jul. 29, 2021

Related U.S. Application Data

(60) Provisional application No. 62/966,086, filed on Jan. 27, 2020.

(51) Int. Cl.
| | |
|---|---|
| *A61M 39/22* | (2006.01) |
| *A61M 5/31* | (2006.01) |
| *F16K 27/06* | (2006.01) |
| *A61M 39/10* | (2006.01) |

(52) U.S. Cl.
CPC .......... *A61M 39/22* (2013.01); *A61M 5/3129* (2013.01); *F16K 27/065* (2013.01); *A61M 2039/1033* (2013.01); *A61M 2039/1083* (2013.01); *A61M 2039/1088* (2013.01); *A61M 2039/229* (2013.01); *A61M 2205/3334* (2013.01); *A61M 2205/581* (2013.01); *A61M 2205/582* (2013.01); *A61M 2205/583* (2013.01); *A61M 2205/6063* (2013.01)

(58) Field of Classification Search
CPC ...... A61M 2039/223; A61M 2039/229; A61M 2205/581; A61M 2205/582; A61M 2205/583; A61M 2205/6063; A61M 39/22; A61M 39/26; A61M 2205/3334
See application file for complete search history.

(56) References Cited

U.S. PATENT DOCUMENTS

| | | | |
|---|---|---|---|
| 9,970,794 B2 | 5/2018 | DeKalb | |
| 2002/0017328 A1* | 2/2002 | Loo | A61M 39/223 137/625.47 |
| 2003/0153897 A1 | 8/2003 | Russo | |

(Continued)

FOREIGN PATENT DOCUMENTS

| | | |
|---|---|---|
| EP | 1627658 B1 | 3/2012 |
| EP | 2777804 A2 | 9/2014 |
| WO | 9934846 A2 | 7/1999 |

*Primary Examiner* — Brandy S Lee
(74) *Attorney, Agent, or Firm* — The Webb Law Firm

(57) ABSTRACT

A medical stopcock includes a main body having an input port and an output port, a valve body having a handle and a syringe port, with the valve body moveable relative to the main body and defining a valve passageway. The valve body includes a first position where the input port and the output port are in fluid communication via the valve passageway, a second position where the syringe port and the output port are in fluid communication via the valve passageway, and a third position where the syringe port and the input port are in fluid communication via the valve passageway. Rotation of the syringe port is configured to move the valve body relative to the main body.

20 Claims, 12 Drawing Sheets

(56) References Cited

U.S. PATENT DOCUMENTS

2007/0287953 A1* 12/2007 Ziv .................... A61M 39/223
                                                      137/605
2015/0202425 A1*  7/2015 Yamamoto .......... A61M 39/223
                                                      600/432
2019/0151569 A1*  5/2019 Fangrow ................ A61M 5/38

* cited by examiner

SYRINGE ACTUATED STOPCOCK SMART-VALVE

CROSS-REFERENCE TO RELATED APPLICATION

The present application claims priority to U.S. Provisional Application Ser. No. 62/966,086, entitled "Syringe Actuated Stopcock Smart-Valve", filed Jan. 27, 2020, the entire disclosure of which is hereby incorporated by reference in its entirety.

BACKGROUND OF THE INVENTION

Field of the Disclosure

The present application relates generally to a medical stopcock.

Description of the Related Art

Stopcocks, such as 3-way stopcocks, include two input ports and one output port. In some configurations, a handle of the stopcock may be operated by a healthcare professional to place the stopcock in three positions, including where a first input port is in fluid communication with the output port, where a second input is in fluid communication with the output port, and where the first input port is in fluid communication with the second input port. Stopcocks are utilized in connection with a variety of situations, including use in connection with a flow sensor system that uses an ultrasonic flowmeter with a flow tube sub-assembly having two piezoelectric transducers coupled to a fluid flow tube. When a transducer is excited by an electrical pulse, ultrasonic waves are transmitted into the fluid and the flow tube. The flow sensor system analyzes the waves traveling through the fluid to determine a velocity, which is proportional to a shift between signals received from the upstream transducer and the downstream transducer.

SUMMARY OF THE INVENTION

In one aspect or embodiment, a medical stopcock includes a main body including an input port and an output port, and a valve body including a handle and a syringe port. The valve body is moveable relative to the main body and defines a valve passageway. The valve body includes a first position where the input port and the output port are in fluid communication via the valve passageway, a second position where the syringe port and the output port are in fluid communication via the valve passageway, and a third position where the syringe port and the input port are in fluid communication via the valve passageway. Rotation of the syringe port is configured to move the valve body relative to the main body.

The syringe port and the valve body may be formed integrally. The syringe port, the valve body, and the handle may be formed integrally. The main body may define a valve opening, with the valve body received within the valve opening. The syringe port may include a threaded connection, with the syringe port configured to rotate the valve body from the first position to the second position when a syringe barrel connected to the threaded connection of the syringe port is rotated. The syringe port may include a female luer connector. The input port may include a female luer connector and the output port may include a male luer connector. The syringe port may include a valve member having a sealed position and an open position, with the valve member of the syringe port to move from the sealed position to the open position when a syringe barrel is secured to the syringe port.

The valve body may include a position structure configured to be sensed by a sensor to determine whether the valve body is in the first position, the second position, or the third position. The position structure may be a recessed portion of the handle of the valve body. The valve body may include at least one indicator to provide an indication of whether the valve body is in the first position, the second position, or the third position.

The valve body may be configured to rotate 180 degrees relative to the main body. The syringe port may be in fluid communication with the input port and the output port when the valve body is in the first position.

The valve passageway may include a first portion, a second portion extending in a first direction perpendicular to the first portion, and a third portion extending in a second direction perpendicular to the first position. The third portion of the valve passageway may be in fluid communication with the syringe port when the valve body is in the first position, the second position, and the third position.

BRIEF DESCRIPTION OF THE DRAWINGS

The above-mentioned and other features and advantages of this disclosure, and the manner of attaining them, will become more apparent and the disclosure itself will be better understood by reference to the following descriptions of aspects of the disclosure taken in conjunction with the accompanying drawings, wherein.

Corresponding reference characters indicate corresponding parts throughout the several views. The exemplifications set out herein illustrate exemplary aspects of the disclosure, and such exemplifications are not to be construed as limiting the scope of the disclosure in any manner.

DETAILED DESCRIPTION

Figure 1:
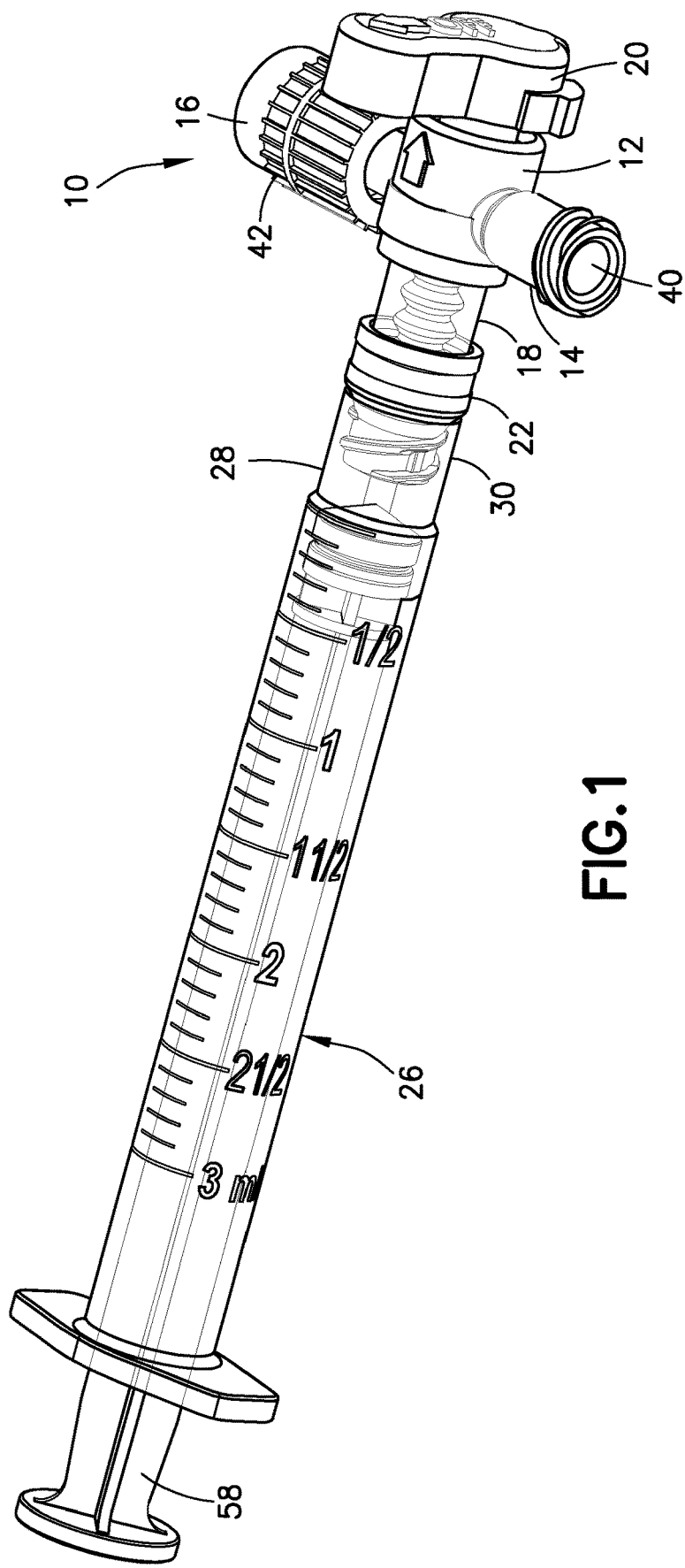
FIG. 1 is a perspective view of a stopcock according to one aspect or embodiment of the present application, showing the stopcock connected to a syringe.
Figure 2:
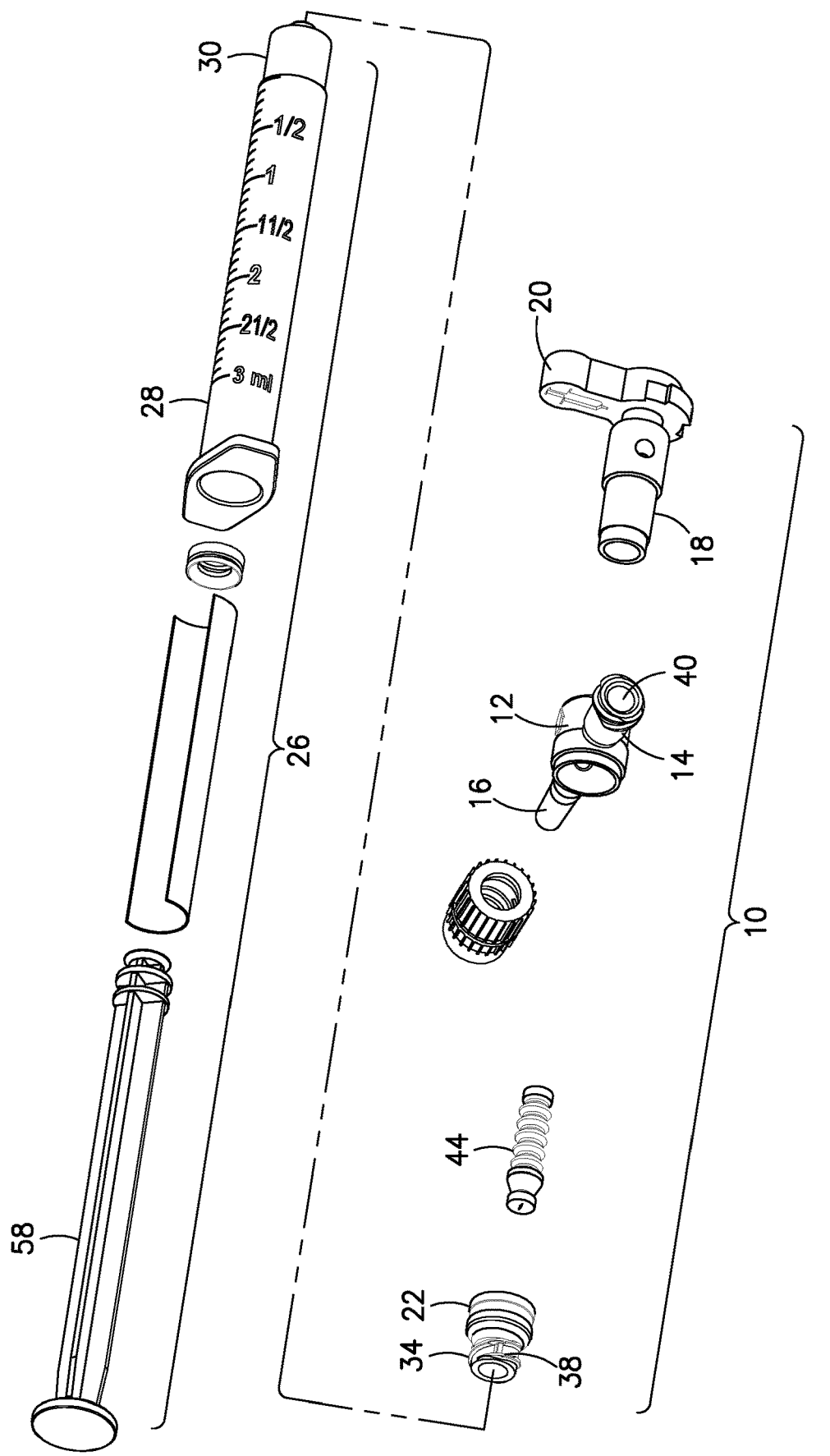
FIG. 2 is an exploded perspective view of the stopcock of FIG. 1.

The following description is provided to enable those skilled in the art to make and use the described aspects contemplated for carrying out the invention. Various modifications, equivalents, variations, and alternatives, however, will remain readily apparent to those skilled in the art. Any and all such modifications, variations, equivalents, and alternatives are intended to fall within the spirit and scope of the present invention.

For purposes of the description hereinafter, the terms "upper", "lower", "right", "left", "vertical", "horizontal", "top", "bottom", "lateral", "longitudinal", and derivatives thereof shall relate to the invention as it is oriented in the drawing figures. However, it is to be understood that the invention may assume various alternative variations, except where expressly specified to the contrary. It is also to be understood that the specific devices illustrated in the attached drawings, and described in the following specification, are simply exemplary aspects of the invention. Hence, specific dimensions and other physical characteristics related to the aspects disclosed herein are not to be considered as limiting. All numbers and ranges used in the specification and claims are to be understood as being modified in all instances by the term "about". By "about" is meant plus or minus twenty-five percent of the stated value, such as plus or minus ten percent of the stated value. However, this should not be considered as limiting to any analysis of the values under the doctrine of equivalents.

Unless otherwise indicated, all ranges or ratios disclosed herein are to be understood to encompass the beginning and ending values and any and all subranges or subratios subsumed therein. For example, a stated range or ratio of "1 to 10" should be considered to include any and all subranges or subratios between (and inclusive of) the minimum value of 1 and the maximum value of 10; that is, all subranges or subratios beginning with a minimum value of 1 or more and ending with a maximum value of 10 or less. The ranges and/or ratios disclosed herein represent the average values over the specified range and/or ratio.

The terms "first", "second", and the like are not intended to refer to any particular order or chronology, but refer to different conditions, properties, or elements.

Referring to FIGS. 1-12, in one aspect or embodiment, a medical stopcock 10 includes a main body 12 having an input port 14 and an output port 16, and a valve body 18 having a handle 20 and a syringe port 22. The valve body 18 is moveable relative to the main body 12 and defines a valve passageway 24. The valve body 18 includes a first position (FIGS. 3 and 4) where the input port 14 and the output port 16 are in fluid communication via the valve passageway 24, a second position (FIGS. 5 and 6) where the syringe port 22 and the output port 16 are in fluid communication via the valve passageway 24, and a third position (FIGS. 7 and 8) where the syringe port 22 and the input port 14 are in fluid communication via the valve passageway 24. Rotation of the syringe port 22 is configured to move the valve body 18 relative to the main body 12, which is discussed in more detail below. In one aspect or embodiment, the syringe port 22 is in fluid communication with the input port 14 and the output port 16 when the valve body 18 is in the first position. In FIGS. 1-8, the stopcock 10 is shown connected to a syringe 26 having a syringe barrel 28 with a male luer connector 30, although other suitable syringes may be utilized. The medical stopcock 10 may be utilized in connection with a flow sensor system, such as the flow sensor system disclosed in U.S. Pat. No. 9,970,794, which is hereby incorporated by reference in its entirety.

Referring to FIGS. 3-8, the syringe port 22, the valve body 18, and the handle 20 are formed integrally. The syringe port 22, the valve body 18, and the handle 20, however, may be formed integrally, may be separately formed, and combinations thereof. The main body 12 defines a valve opening 32, with the valve body 18 received within the valve opening 32.

Referring again to FIGS. 1-12, the syringe port 22 includes a threaded connection 34, with the syringe port 22 configured to rotate the valve body 18 from the first position to the second position when the syringe barrel 28 connected to the threaded connection 34 of the syringe port 22 is rotated. Therefore, a healthcare professional can move the valve body 18 from the first position to the second position via the syringe 26. In other words, once the threaded connection 34 of the syringe port 22 is engaged with the luer connector 30 of the syringe barrel 28, further rotation of the syringe barrel 28, such as a clockwise rotational direction, causes the valve body 18 to rotate relative to the main body 12 with the valve body 18 moving from the first position to the second position. In one aspect or embodiment, the threaded connection 34 of the syringe port 22 is a two-start thread, which can be aligned one-half turn apart as a starting position such that the syringe barrel 28 may be secured to the threaded connection 34 by rotating the syringe 26 180 degrees clockwise until the connection is secured. Further rotation of the syringe 26 90 degrees clockwise moves the valve body 18 from the first position to the second position. A healthcare professional may move the valve body 18 to and from each of the first position, the second position, and the third position using the handle 20 of the valve body 18. In one embodiment or aspect, the valve body 18 and the valve opening 32 of the main body 12 have a tight fit, which may require a user to use the handle 20 to move the valve body 18. In one embodiment or aspect, the valve body 18 and the valve opening 32 of the main body 12 have a loose fit, which facilitates movement of the valve body 18 via the syringe 26 when the syringe 26 is connected to the syringe port 22.

In one aspect or embodiment, the valve body 18 and/or main body 12 includes an indicator structure (not shown) to provide an audible and/or tactile indication when the valve body 18 is in the first position. An audible and/or tactile indication may also be provided when the valve body 18 reaches the second and third positions. In one aspect or embodiment, the valve body 18 and/or main body 12 includes one or more stops (not shown) to restrict movement of the valve body 18 to movement between the first position, the second position, and the third position. In one aspect or embodiment, the valve body 18 is configured to rotate 180 degrees relative to the main body 12.

Referring to FIGS. 3-8, the syringe port 22 includes a female luer connector 38, although other suitable connectors may be utilized. The input port 14 includes a female luer connector 40 and the output port 16 includes a male luer connector 42 with a spinning luer lock, although other suitable connectors may be utilized. The syringe port 22 includes a valve member 44 having a sealed position and an open position, with the valve member 44 configured to move from the sealed position to the open position when the syringe 26 is secured to the syringe port 22. Although not shown in FIGS. 1-8, when the syringe 26 is connected to the syringe port 22, the male luer connector 30 of the syringe 26 engages the valve member 44 of the syringe port 22 to move or retract the valve member 44 from the sealed position to the open position thereby placing the syringe barrel 28 in fluid communication with the syringe port 22.

Figure 3:
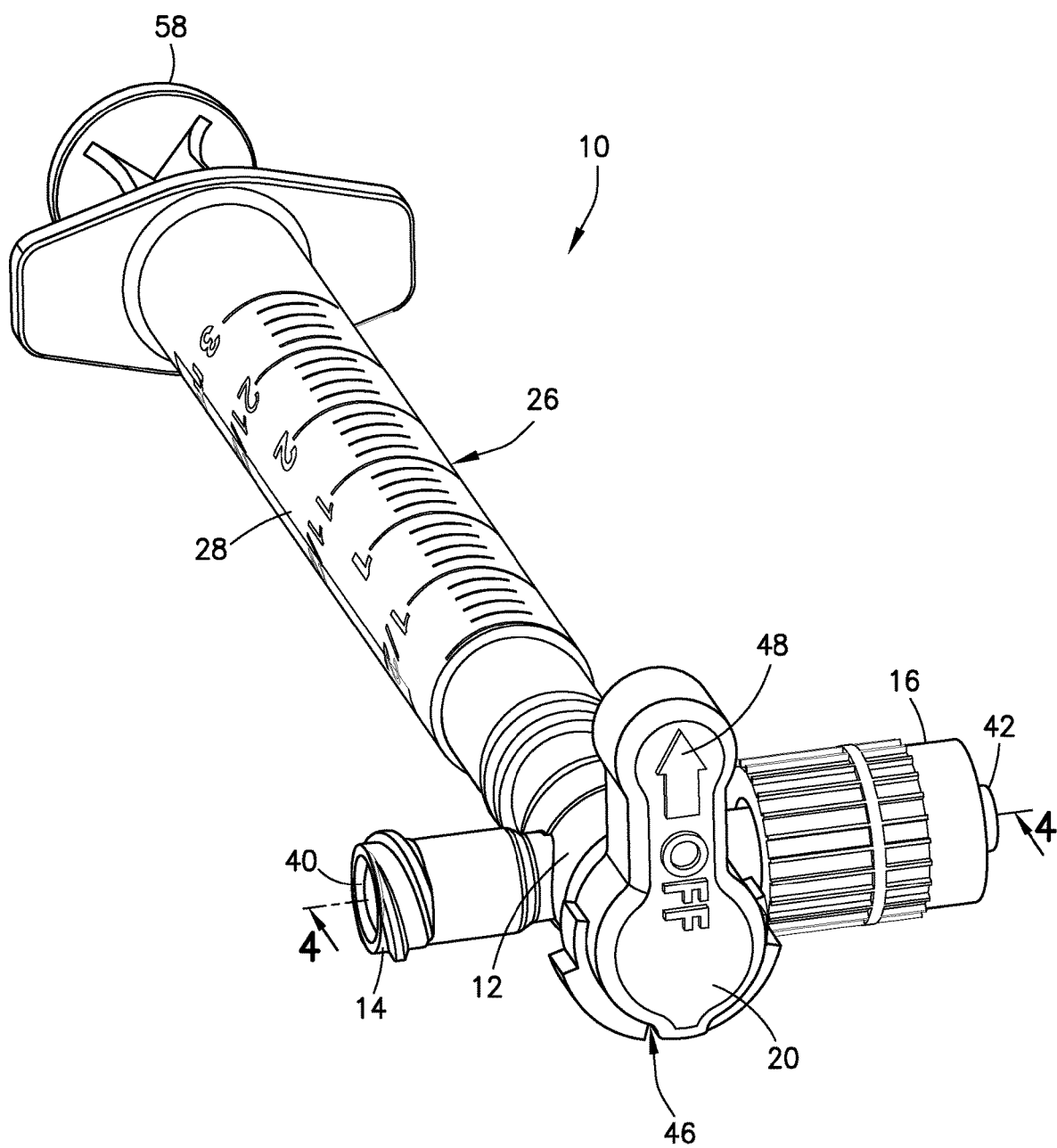
FIG. 3 is a bottom perspective view of the stopcock of FIG. 1, showing a first position of the stopcock.
Figure 4:
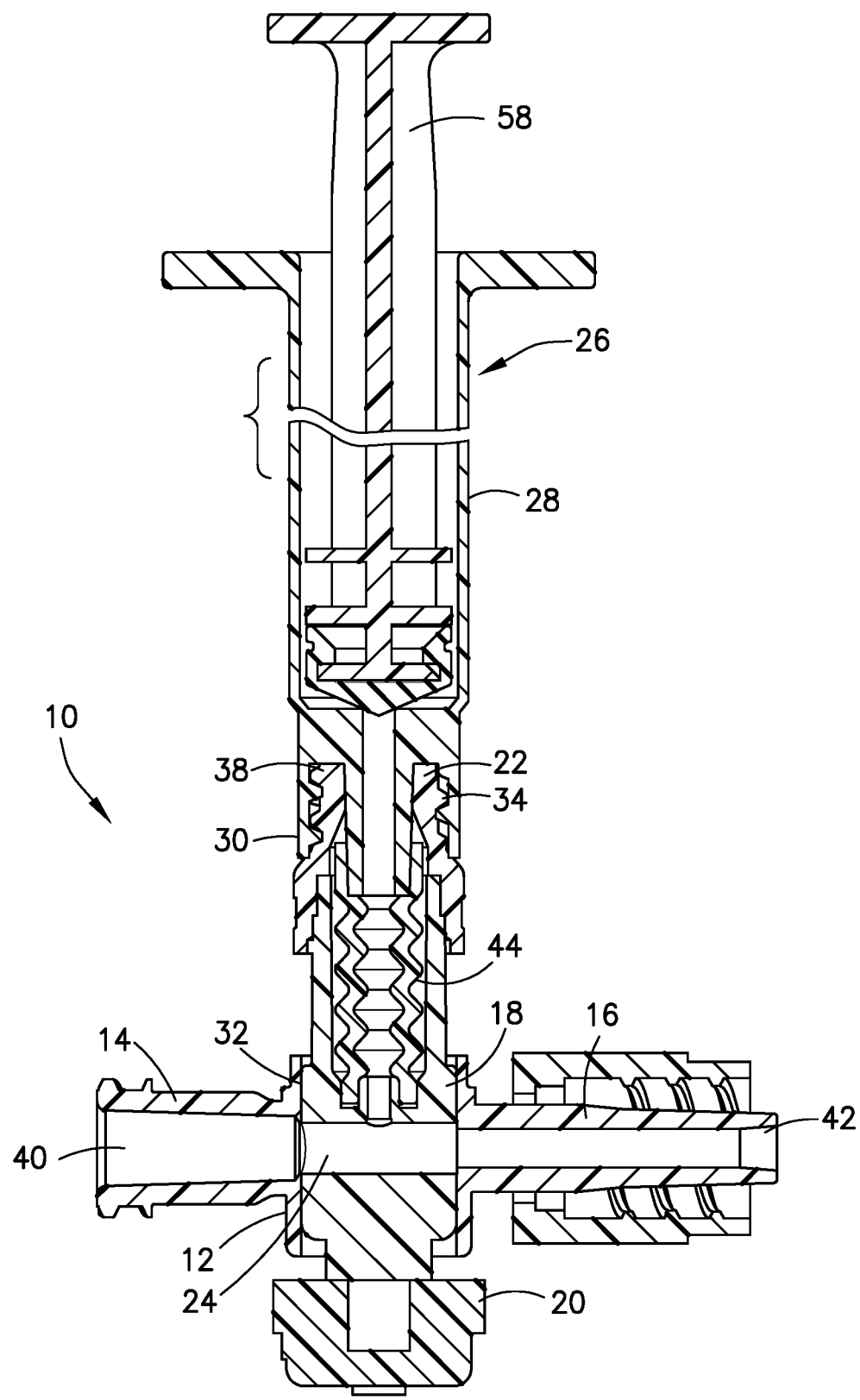
FIG. 4 is a cross-sectional view along line 4-4 in FIG. 3.
Figure 5:
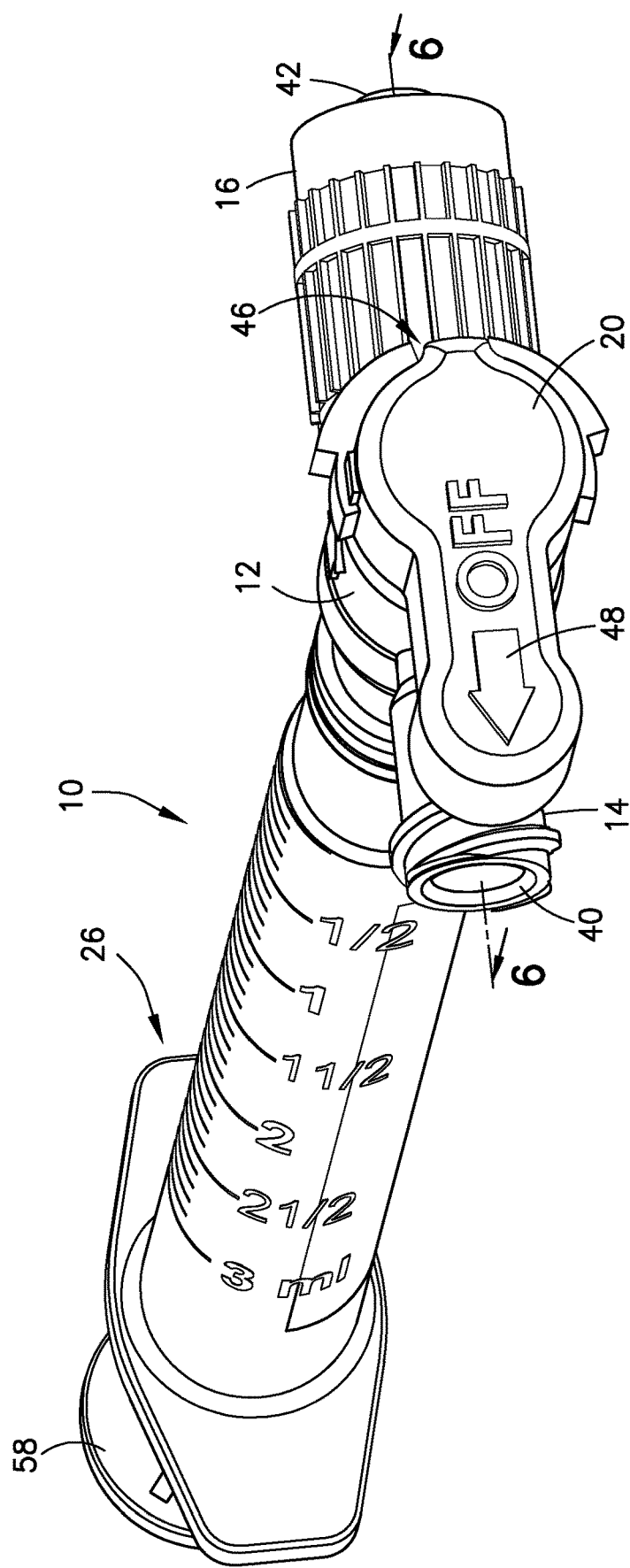
FIG. 5 is a bottom perspective view of the stopcock of FIG. 1, showing a second position of the stopcock.
Figure 6:
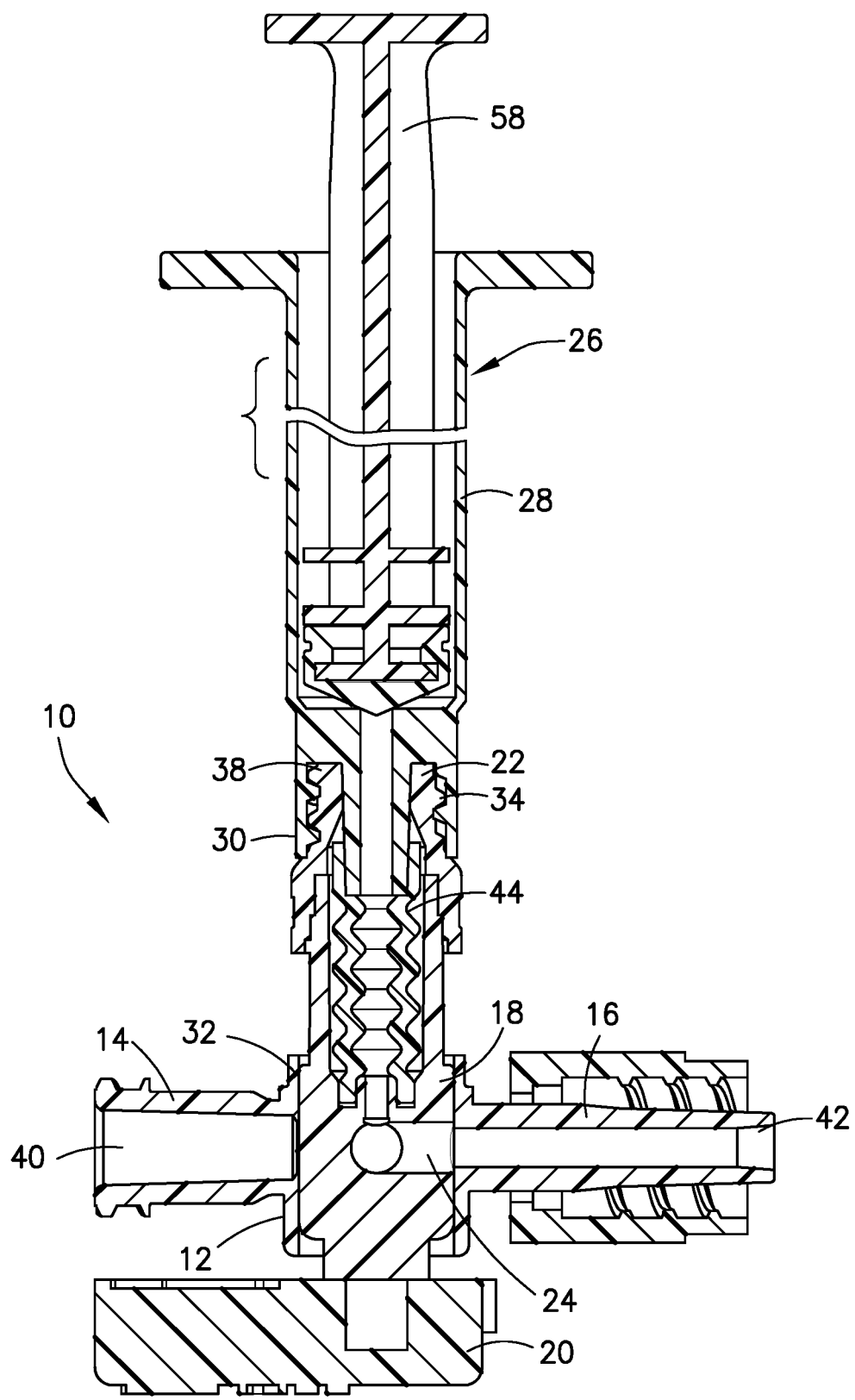
FIG. 6 is a cross-sectional view along line 6-6 in FIG. 5.
Figure 7:
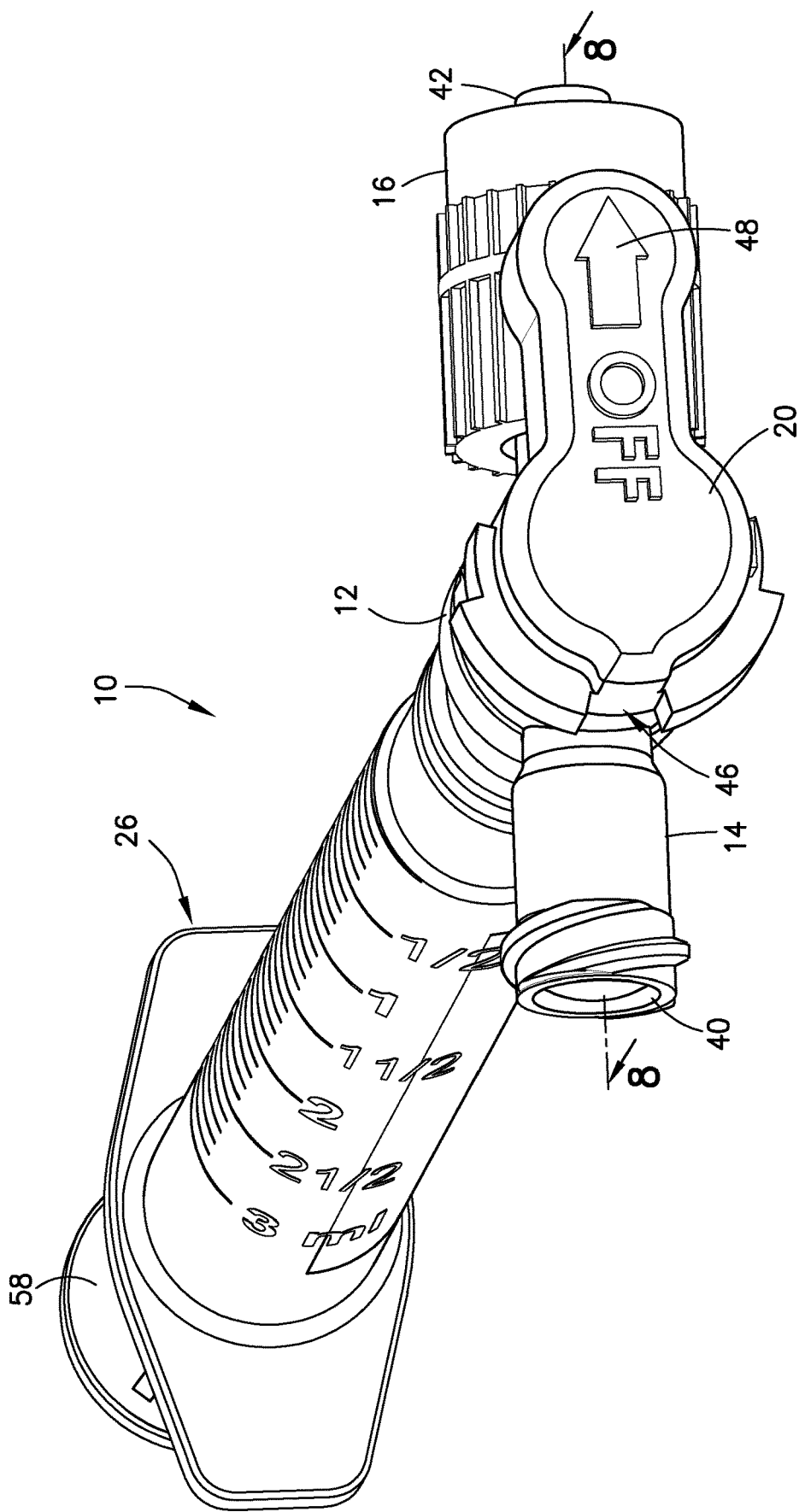
FIG. 7 is a bottom perspective view of the stopcock of FIG. 1, showing a third position of the stopcock.
Figure 8:
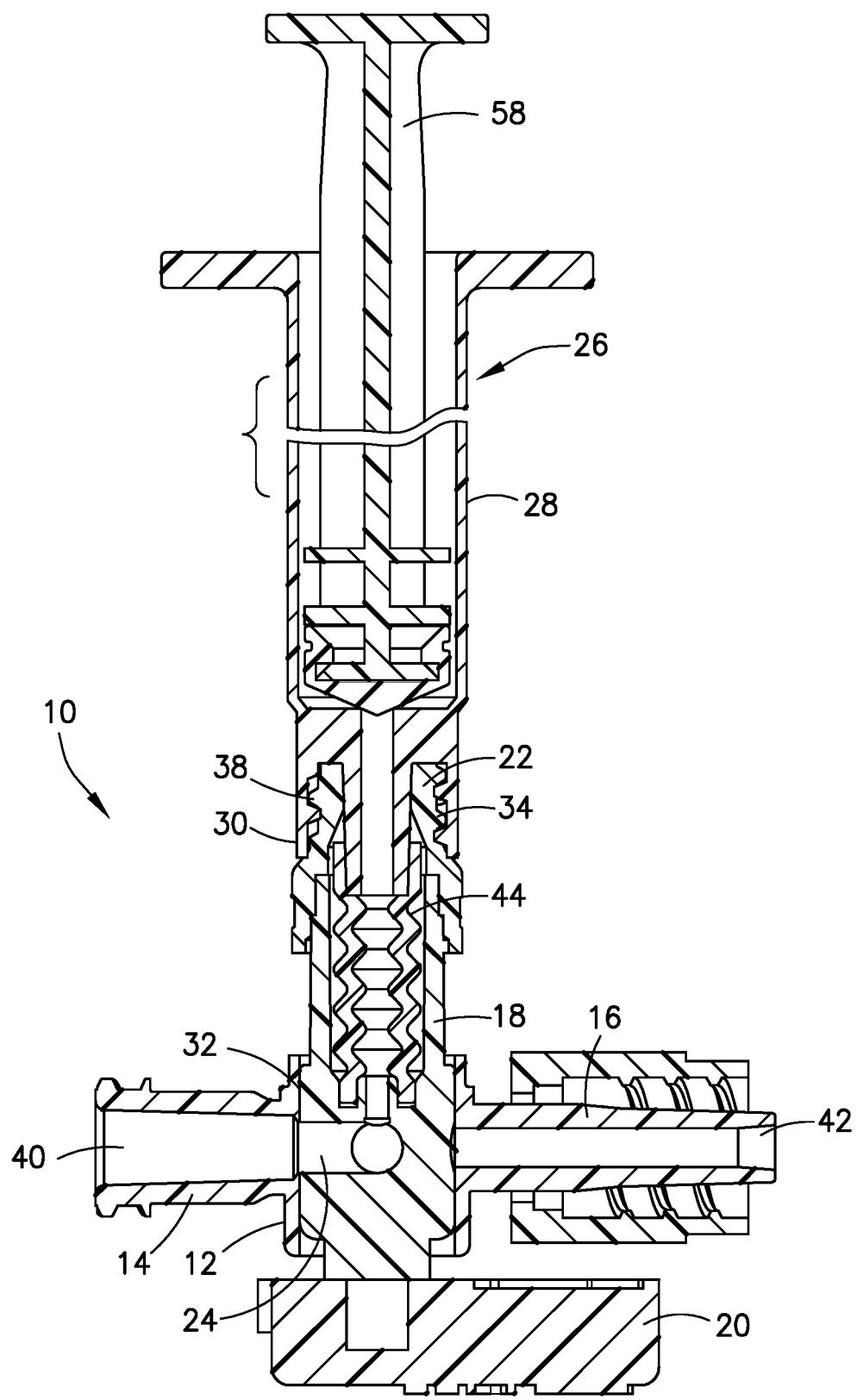
FIG. 8 is a cross-sectional view along line 8-8 in FIG. 7.
Figure 9:
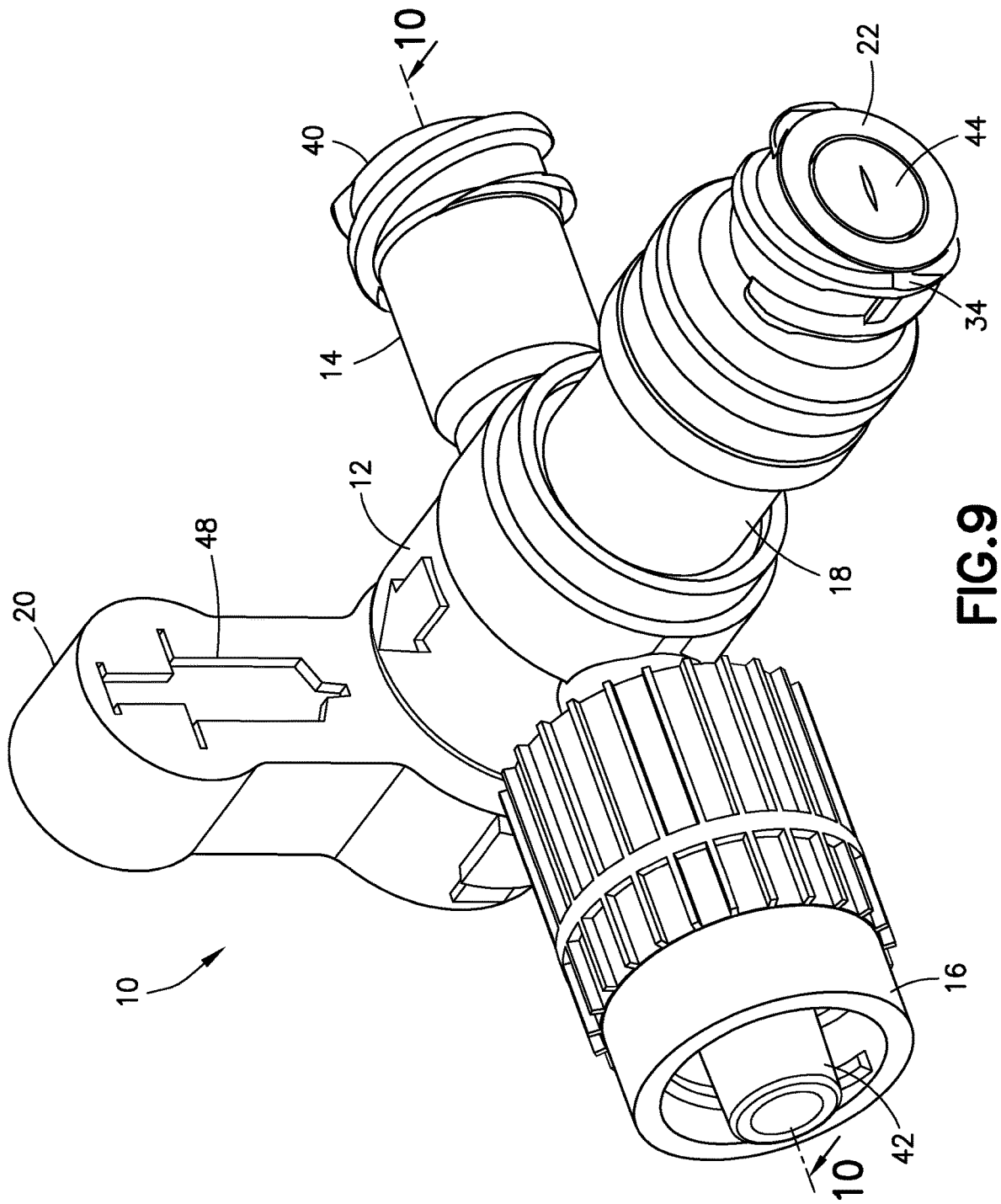
FIG. 9 is a top perspective view of the stopcock of FIG. 1.
Figure 10:
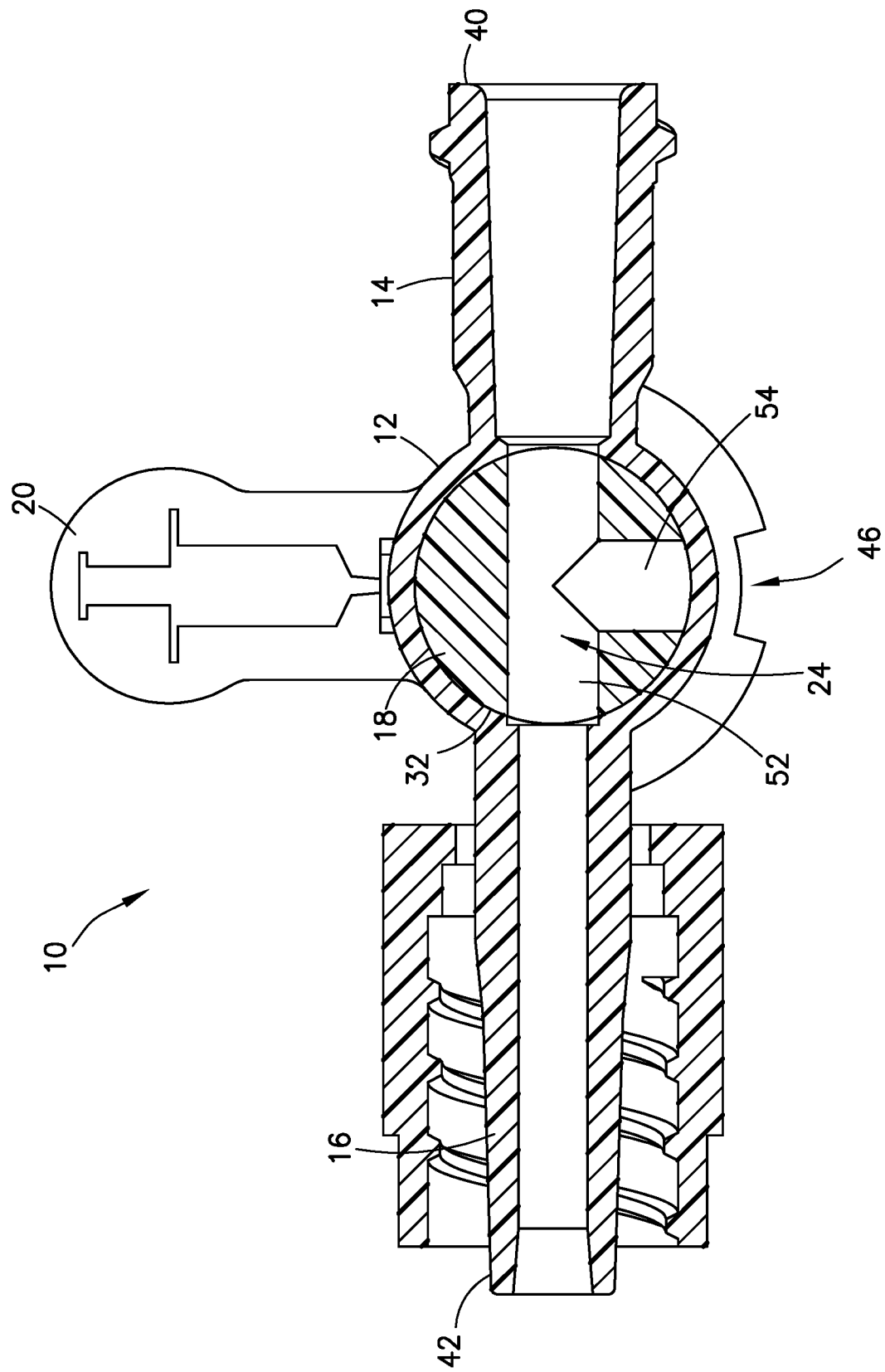
FIG. 10 is a cross-sectional view taken along line 10-10 in FIG. 9.
Figure 11:
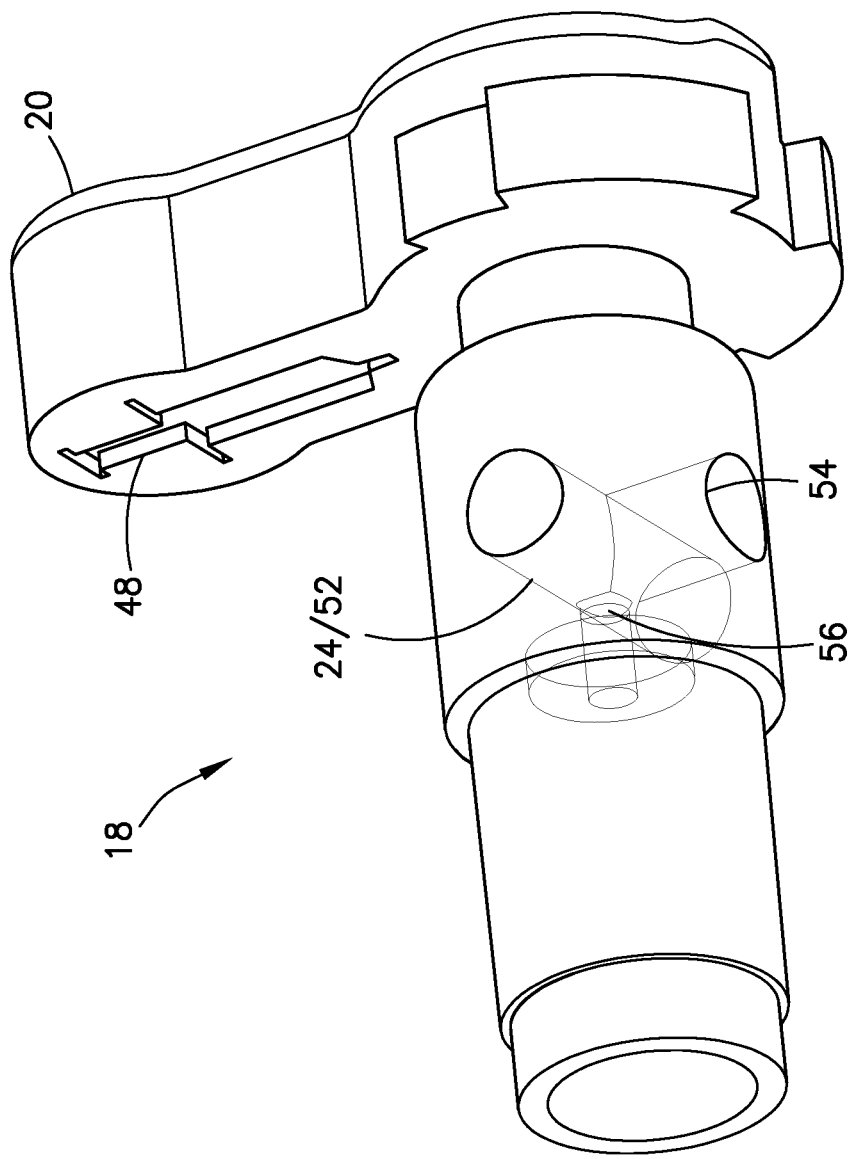
FIG. 11 is a right-side perspective view of a valve body of the stopcock of FIG. 1 with a portion of the valve body being transparent for clarity.
Figure 12:
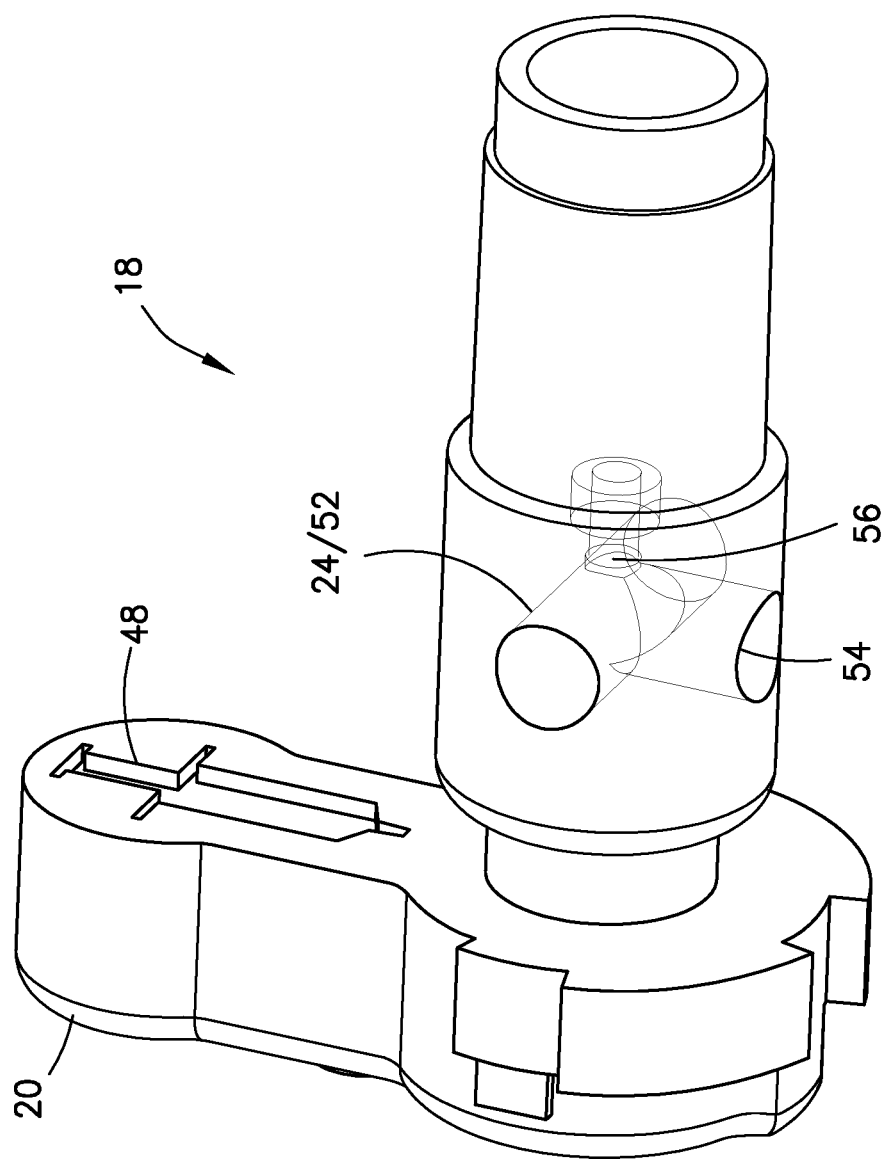
FIG. 12 is a left-side perspective view of a valve body of the stopcock of FIG. 1 with a portion of the valve body being transparent for clarity.

Referring to FIGS. 3, 5, and 7, the valve body 18 includes a position structure 46 configured to be sensed by a sensor to determine whether the valve body 18 is in the first position, the second position, or the third position. In one aspect or embodiment, the position structure 46 is a recessed portion of the handle 20 of the valve body 18. The position structure 46 may act as a flag or shutter that can be sensed by an external sensor or mechanism to determine the position of the valve body 18. The valve body 18 includes at least one visual indicator 48 to provide an indication of whether the valve body 18 is in the first position, the second position, or the third position. The visual indicator 48 may be an arrow, text, shape of the handle 20, or any other suitable indication arrangement.

Referring to FIGS. 9-12, the valve passageway 24 includes a first portion 52, a second portion 54 extending in a first direction perpendicular to the first portion 52, and a third portion 56 extending in a second direction perpendicular to the first portion 52. The third portion 56 of the valve passageway 24 is in fluid communication with the syringe port 22 when the valve body 18 is in the first position, the second position, and the third position.

In a further aspect or embodiment of the present application, a method of using the stopcock 10 includes: securing the syringe 26 to the syringe port 22 and continuing to rotate the syringe 26 until the valve body 18 of the stopcock 10 moves from the first position to the second position; performing an injection with fluid being transferred from the syringe 26 to the output port 16; and returning the valve body 18 to the first position using the handle 20 of the valve body 18.

In one aspect or embodiment, the method further includes: moving the valve body 18 to the third position using the handle 20 of the valve body 18; retracting a plunger 58 of the syringe 26 to draw fluid from an IV line (not shown) connected to the input port 14 into the syringe barrel 28; and injecting saline flush fluid using the syringe 26 to force fluid through the output port 16. The syringe 26 may be disconnected from the syringe port 22 by rotating the syringe 26 in a counterclockwise direction.

While this disclosure has been described as having exemplary designs, the present disclosure can be further modified within the spirit and scope of this disclosure. This application is therefore intended to cover any variations, uses, or adaptations of the disclosure using its general principles. To the extent possible, one or more features of any embodiment or aspect can be combined with one or more features of any other embodiment or aspect. Further, this application is intended to cover such departures from the present disclosure as come within known or customary practice in the art to which this disclosure pertains and which fall within the limits of the appended claims.

What is claimed is:

1. A medical stopcock comprising:
a main body consisting of only one input port and only one output port; and
a valve body comprising a handle and only one syringe port, where the valve body is moveable relative to the main body and defines a valve passageway, and where movement of the valve body consists of three positions permitting fluid flow, a first position where the one input port and the one output port are in fluid communication via the valve passageway, a second position where the one syringe port and the one output port are in fluid communication via the valve passageway, and a third position where the one syringe port and the one input port are in fluid communication via the valve passageway, wherein rotation of the syringe port is configured to move the valve body relative to the main body,
wherein the valve body comprises a position structure configured to be sensed by a position sensor to determine whether the valve body is in the first position, the second position, or the third position,
wherein the position structure comprises a portion of the handle of the valve body,
wherein the medical stopcock further comprises a flow sensor to determine fluid flow velocity through the medical stopcock,
wherein movement of the valve body from the first position to the second position permits fluid to be transferred from the one syringe port to the one output port,
wherein movement of the valve body from the first position to the third position permits fluid to be drawn from the one input port to the one syringe port, and
wherein the valve passageway comprises a first portion, a second portion extending in a first direction perpendicular to the first portion, and a third portion extending in a second direction perpendicular to the first position, with all of the first portion, the second portion, and the third portion fluidly connected with each other.

2. The medical stopcock of claim 1, wherein the syringe port and the valve body are formed integrally.

3. The medical stopcock of claim 2, wherein the syringe port, the valve body, and the handle are formed integrally.

4. The medical stopcock of claim 1, wherein the main body defines a valve opening, and wherein the valve body is received within the valve opening.

5. The medical stopcock of claim 1, wherein the syringe port comprises a threaded connection, and wherein the syringe port is configured to rotate the valve body from the first position to the second position when a syringe barrel connected to the threaded connection of the syringe port is rotated.

6. The medical stopcock of claim 1, wherein the syringe port comprises a female luer connector.

7. The medical stopcock of claim 1, wherein the input port comprises a female luer connector and the output port comprises a male luer connector.

8. The medical stopcock of claim 1, wherein the syringe port comprises a valve member having a sealed position and an open position, the valve member of the syringe port is configured to move from the sealed position to the open position when the syringe barrel is secured to the syringe port.

9. The medical stopcock of claim 1, wherein the position structure comprises a recessed portion of the handle of the valve body.

10. The medical stopcock of claim 1, wherein the valve body includes at least one indicator to provide an indication of whether the valve body is in the first position, the second position, or the third position.

11. The medical stopcock of claim 1, wherein the valve body is configured to rotate 180 degrees relative to the main body.

12. The medical stopcock of claim 1, wherein the syringe port is in fluid communication with the input port and the output port when the valve body is in the first position.

13. The medical stopcock of claim 1, wherein the third portion of the valve passageway is in fluid communication with the syringe port when the valve body is in the first position, the second position, and the third position.

14. A medical stopcock comprising:
a main body consisting of an input port and an output port; and a valve body comprising a handle and syringe port, where the valve body is moveable relative to the main body and defines a valve passageway, and where movement of the valve body includes a first position where the syringe port and the output port are in fluid communication via the valve passageway, and a second position where the syringe port and the input port are in fluid communication via the valve passageway, wherein rotation of the syringe port is configured to move the valve body relative to the main body, wherein the valve body and the valve passageway are designed to permit connection of only one of the input port or the output port to the syringe port at the same time, and wherein the valve passageway comprises a first portion, a second portion extending in a first direction perpendicular to the first portion, and a third portion extending in a second direction perpendicular to the first position, with all of the first portion, the second portion, and the third portion fluidly connected with each other.

15. The medical stopcock of claim 14, wherein the syringe port and the valve body are formed integrally.

16. The medical stopcock of claim 14, wherein the main body defines a valve opening, and wherein the valve body is received within the valve opening.

17. The medical stopcock of claim 14, wherein the syringe port comprises a threaded connection, and wherein the syringe port is configured to rotate the valve body from the first position to the second position when a syringe barrel connected to the threaded connection of the syringe port is rotated.

18. The medical stopcock of claim 14, wherein the syringe port comprises a female luer connector.

19. The medical stopcock of claim 14, wherein the input port comprises a female luer connector and the output port comprises a male luer connector.

20. The medical stopcock of claim 14, wherein the valve body includes at least one indicator to provide an indication of whether the valve body is in the first position, the second position, or the third position.

* * * * *